United States Patent [19]

Trick et al.

[11] Patent Number: 4,726,360

[45] Date of Patent: Feb. 23, 1988

[54] PENILE PROSTHESIS

[75] Inventors: Robert E. Trick, Racine; Steven M. Miles, West Allis, both of Wis.

[73] Assignee: Medical Engineering Corporation, Racine, Wis.

[21] Appl. No.: 887,069

[22] Filed: Jul. 17, 1986

[51] Int. Cl.⁴ .............................................. A61F 2/26
[52] U.S. Cl. ...................................................... 128/79
[58] Field of Search ............................................ 128/79

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,201,202 | 5/1980 | Finney et al. | 128/79 |
| 4,267,829 | 5/1981 | Burton et al. | 128/79 |
| 4,318,396 | 3/1982 | Finney | 128/79 |
| 4,342,308 | 8/1982 | Trick | 128/79 |
| 4,353,360 | 10/1982 | Finney et al. | 128/79 |
| 4,360,010 | 11/1982 | Finney | 128/79 |
| 4,364,379 | 12/1982 | Finney | 128/79 |
| 4,369,771 | 1/1983 | Trick | 128/79 |
| 4,383,525 | 5/1983 | Scott et al. | 128/79 |
| 4,399,811 | 8/1983 | Finney et al. | 128/79 |
| 4,399,812 | 8/1983 | Whitehead | 128/79 |
| 4,550,719 | 11/1985 | Finney et al. | 128/79 |
| 4,574,792 | 3/1986 | Trick | 128/79 |
| 4,590,927 | 5/1986 | Porter et al. | 128/79 |
| 4,602,625 | 7/1986 | Yachia et al. | 128/79 |
| 4,622,958 | 11/1986 | Finney | 128/79 |

FOREIGN PATENT DOCUMENTS

WO80/00302  3/1980  PCT Int'l Appl. .............. 128/79

*Primary Examiner*—Gene Mancene
*Assistant Examiner*—Cary E. Stone
*Attorney, Agent, or Firm*—Quarles & Brady

[57] ABSTRACT

A penile prosthesis which is adapted to be surgically implanted in man for the treatment of erectile impotence includes at least one elongated, flexible cylindrical member which is adapted to be implanted into the corpus cavernosum of the pendulous penis, a pressure bulb for pressurizing liquid and tubing connecting the member and the bulb. The member includes an inner non-distensible pressure chamber and an outer distensible chamber. The two chambers are connected by a passage and a valve for controlling flow through the passage so that fluid can be transferred from the pressure bulb via the pressure chamber to the outer chamber to cause it to distend and in turn increase penile girth.

2 Claims, 8 Drawing Figures

PENILE PROSTHESIS

FIELD OF THE INVENTION

The present invention relates to penile prostheses for curing erectile impotence. More particularly, it relates to an inflatable penile implant.

BACKGROUND OF THE INVENTION

In some instances of erectile impotence in which the patient does not respond to more conventional therapy, the surgical implanting of a penile prosthesis may be the only practical means of remedying the impotency.

In the past, several types of penile prostheses have been employed. The first type is a pair of rods of suitable stiffness each of which is surgically implanted into a corpus cavernosum of the penis. One disadvantage of the rod-type implant is that the stiffness of the rods makes it difficult to implant rods of sufficient diameter so that the penis in the erectile state will have normal girth. The sleeve prosthesis disclosed in U.S. Pat. No. 4,204,350 is an attempt to overcome that disadvantage.

The other type of penile prosthesis which is available is the inflatable prosthesis. The most common inflatable prosthesis includes two fairly long inflatable distensible tubes that are surgically implanted in the corpora cavernosa of the penis. Each of the two tubes is connected by tubing to a pressure bulb of inflating fluid which is implanted elsewhere in the body. The distensible tubes are collapsible so that they can be easily implanted and they can be inflated to increase the girth of the penis to that attained in a normal erection. However, because of the large volume required to pressurize and rigidize the inflatable tubes, the pressure bulbs can be relatively large. In the prosthesis of U.S. Pat. No. 3,954,102, the pressure bulbs are relatively small and the pressurizing fluid is supplied from a single relatively large reservoir which is implanted in the abdominal cavity.

Another type of inflatable penile prosthesis that can result in increased girth is that of U.S. Pat. No. 4,009,711. It comprises two implants each having its own relatively large pressurizing bulb which is surgically implanted in the scrotal sac. Each implant includes a non-distensible stem portion made of a relatively stiff material to support the implant and an integral collapsible balloon-like distensible portion which is implanted into the corpora of the pendulous penis and inflated to affect an erection.

Still another type of inflatable penile prosthesis that can be used to increase girth is that disclosed in U.S. Pat. No. 4,201,202. It comprises a pair of rod-type implants each having an inflatable sleeve attached about the rod portion to form an inflatable chamber and a pressure bulb for inflating the chamber.

More recently, patents have issued describing penile implants which can be implanted completely in the penis. Such implants are cylindrical members having self-contained pumps, reservoirs and pressure chambers. The pressure chambers are non-distensible so that only a small amount of fluid is needed to be transferred to make the pressure chamber rigid. However, like the rod-type implants these inflatable implants do not increase the girth of the penis. Representative of such implants are those shown in U.S. Pat. No. 4,353,360.

There are a number of patients suffering from erectile dysfunction which are not satisfied with the prior art rod-type implants or the inflatable penile implants because they either do not increase the penile girth or else they require too extensive surgery, or require too large pressure bulbs.

It obviously would be desirable to have a simple implant in which the penile girth could be increased and preferably one which did not require extensive surgery to implant or large pressure bulbs.

SUMMARY OF THE INVENTION

It is the general object of the present invention to disclose an improved inflatable penile prosthesis with means for increasing the girth of the penis.

It is a further object to disclose such an implant which does not require extensive surgery or large pressure bulbs.

It also is an object to disclose an implant in which the penile girth can be variably adjusted.

The present invention comprises a penile implant including an elongated, flexible, cylindrical member having a pressure chamber which is adapted to be implanted in the corpus cavernosum of the penis, a pressure bulb for inflating the pressure chamber in the cylinder and tubing connecting the bulb to the pressure chamber.

The implant of the present invention differs from prior art devices in that the inflatable member contains an inner non-distensible cylindrical pressure chamber, an outer distensible, cylindrical chamber positioned radially about the inner chamber, a passage connecting the inner and outer chambers, and first valve means for controlling flow of liquid from the inner pressure chamber to the outer chamber to increase penile girth. The implant also has a second valve means for controlling the flow of the pressurizing liquid between the pressure bulb and the pressure chamber. A complete prosthesis preferably comprises two separate cylinders each sharing a common pressure bulb which is adapted to be implanted into the scrotal sac.

In a preferred embodiment the cylindrical member is provided with a relatively stiff, proximal end which is adapted to be implanted into the root end of the corpus cavernosum to anchor and support the implant and the distal portion cylindrical member contains the inner and outer chambers and is adapted to be implanted into a corpus cavernosum of the pendulus penis. The more flexible, soft distal portion causes a minimum of irritation to the tissue of the penis and permits the pendulus penis to assume a normal position when the implant is not inflated. In an especially preferred embodiment, the distal tip of the cylinder is shaped to fit the end of the corpus cavernosum and it includes the first valve means.

The penile implant of the present invention provides a unique feature over previously available inflatable implants; it permits the variable adjustment of the girth of the penis. This is an important advantage for patients desiring a normal appearing erectile penis. The implant of the present invention can be implanted and after the patient is completely healed the non-distensible pressure chamber can be pressurized with liquid from the pressure blub like prior art implants to effect a penile erection. However, if the girth of the penis is smaller than desired the girth then can be effectively increased to a more acceptable level by transferring liquid from the pressure chamber to the distensible outer chamber. This is done by opening the first valve means by deforming the first valve housing while simultaneously exerting pressure on the pressure bulb.

DESCRIPTION OF THE PREFERRED EMBODIMENT

Figure 1:
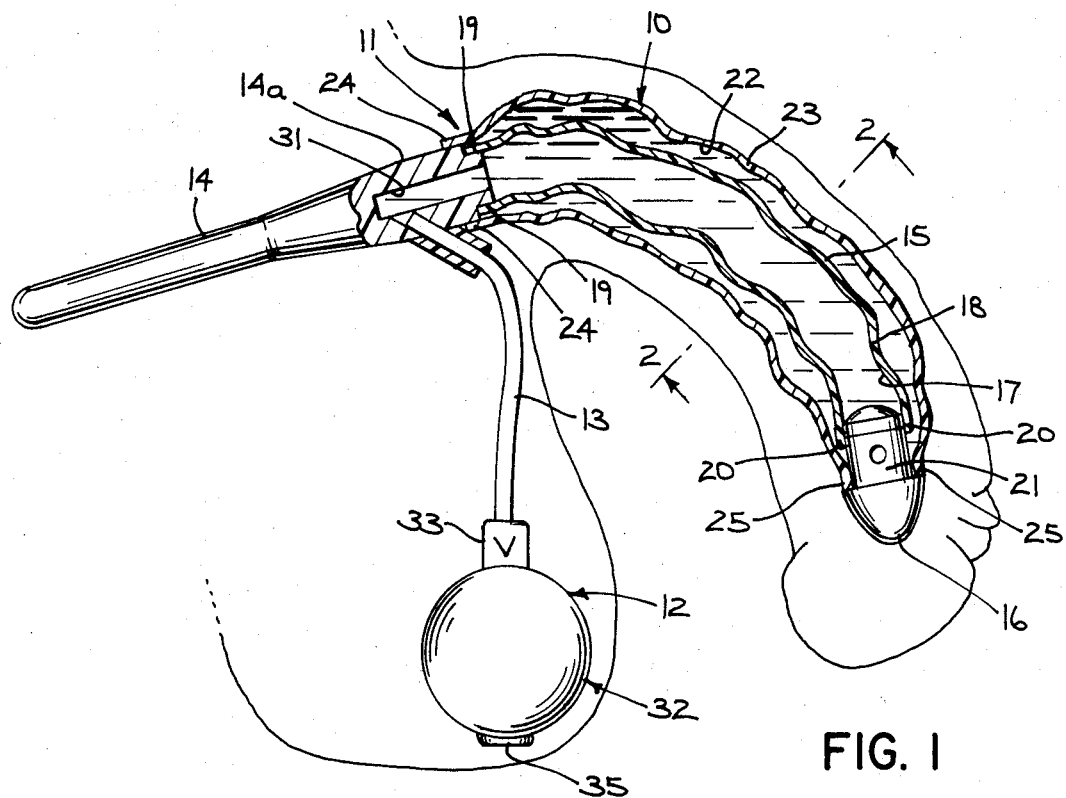
FIG. 1 is a partial sectional view of the penile prosthesis of the present invention in a depressurized condition as surgically implanted in a male.
Figure 4:
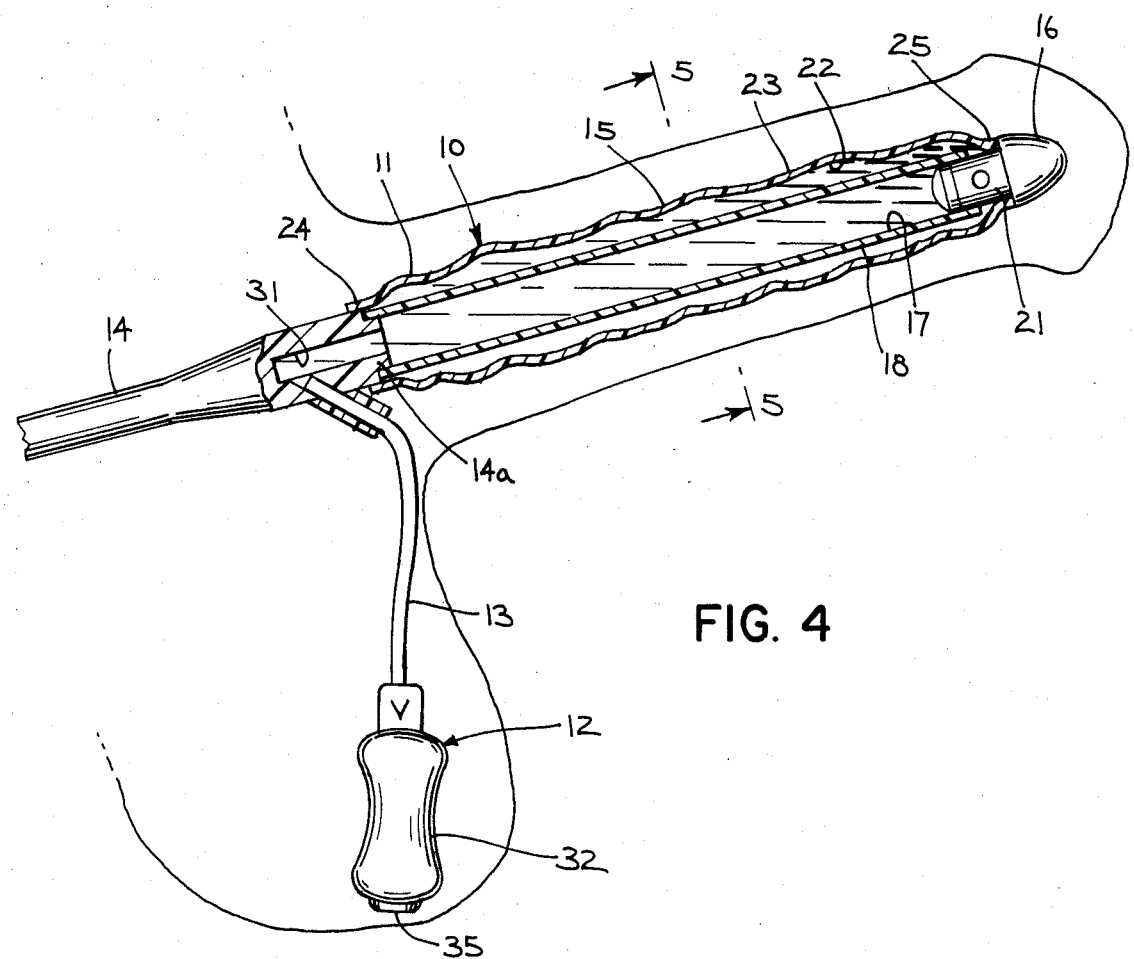
FIG. 4 is a view similar to FIG. 1, except the prosthesis is fully pressurized.
Figure 6:
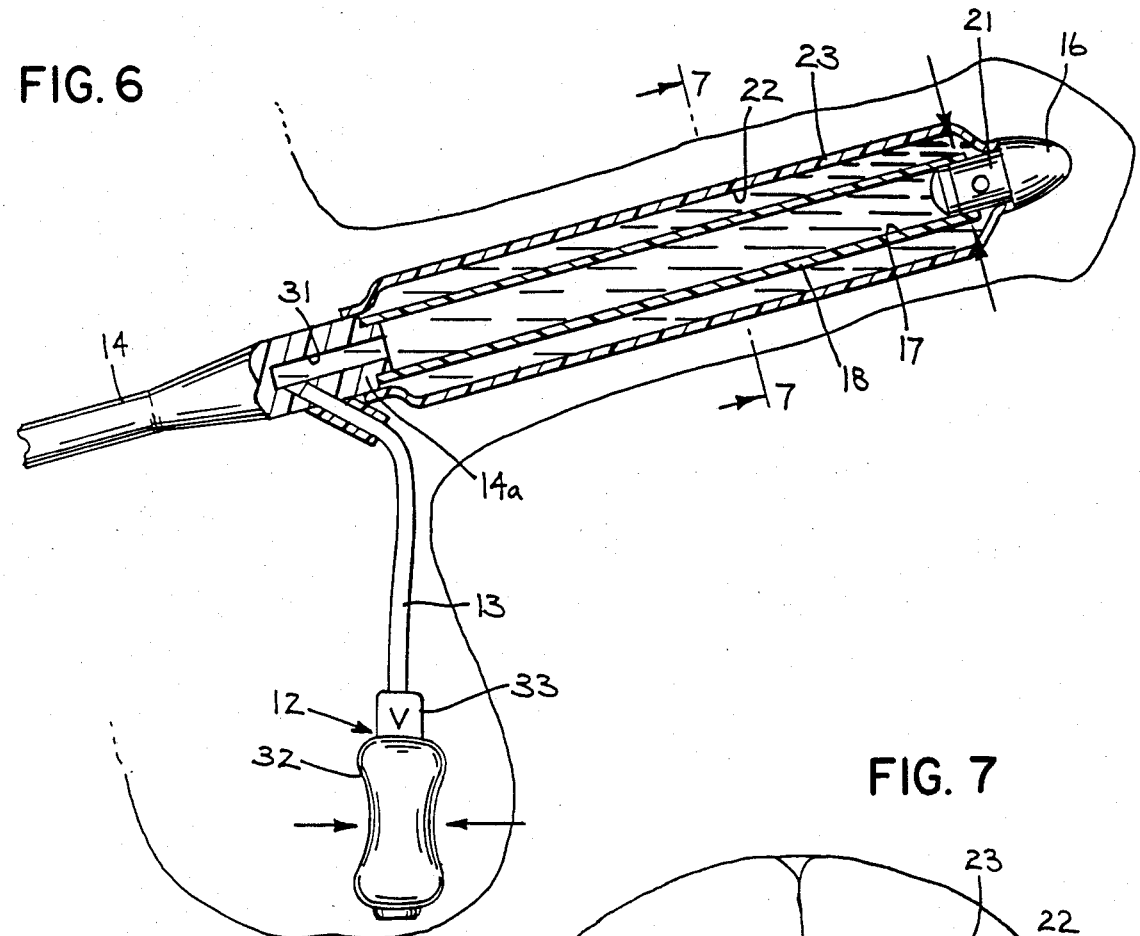
FIG. 6 is a view similar to FIG. 1 but showing liquid being transferred to the outer cylinder to increase girth.

As seen in FIGS. 1, 4 and 6 of the drawings, the preferred penile implant 10 comprises an elongated cylindrical member 11, a pressure bulb assembly 12 and tubing 13 connecting the bulb 12 to the member 11. The member 11 is provided with a short, proximal portion or stem 14 of relatively stiff material which is implanted in the root end of a corpus cavernosum to support and anchor the implant, and a longer distal portion 15 of the member 11 which is of a softer, more flexible material and which is implanted into the portion of corpus cavernosum in the pendulous penis. The distal portion 15 is provided with a tip 16 which is paraboloidal in shape to conform to the inner shape of the end of the corpus cavernosum.

Positioned within the distal portion 15 is a pressure chamber 17 which is formed of an inner sleeve 18 of non-distensible, preferably silicone coated fabric material. The sleeve 18 is sealed at one end 19 to the inner end 14a of the stem 14 and at the other end 20 to a valve block 21 in a fluid-tight manner. The seals between the ends 19 and 20 of the sleeve 18 and the stem 14 and valve block 21 are preferably made with a suitable silicone adhesive.

Figure 2:
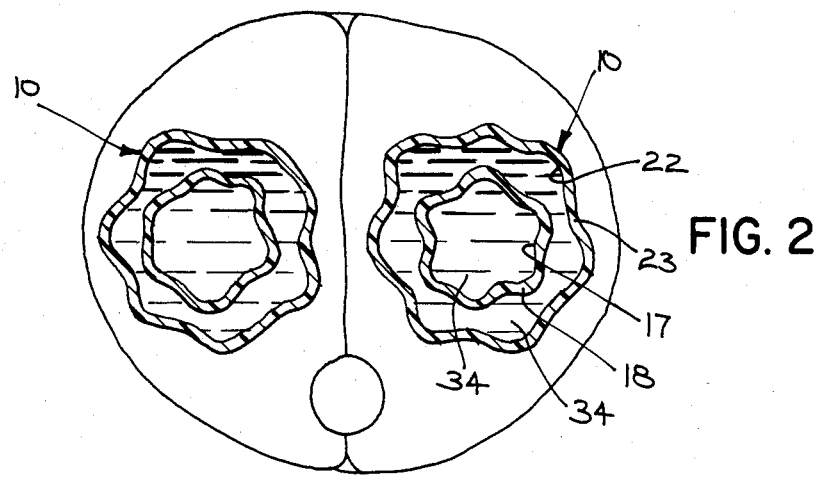
FIG. 2 is a cross sectional view taken along the lines 2—2 in FIG. 1.
Figure 5:
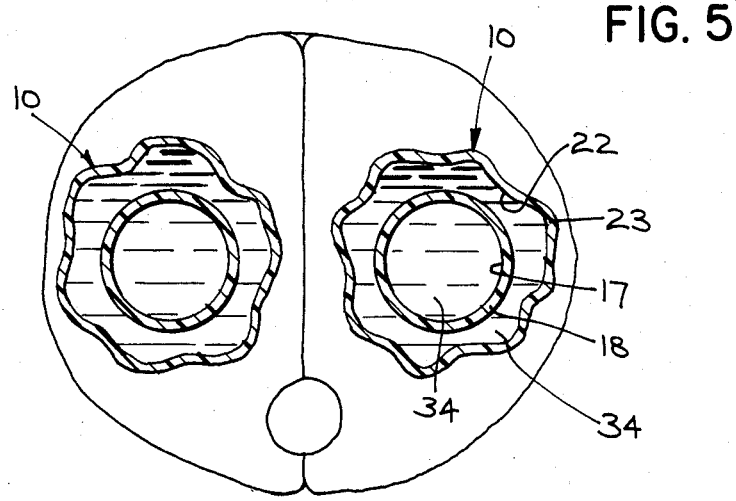
FIG. 5 is a view taken along line 5—5 in FIG. 4.
Figure 7:
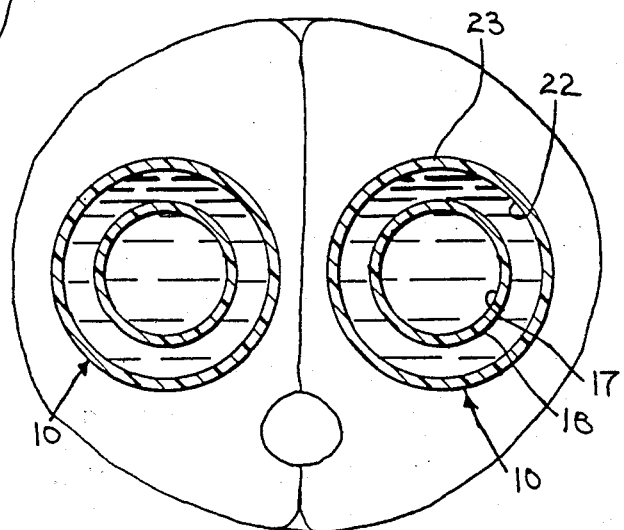
FIG. 7 is a view taken along line 7—7 in FIG. 6.

As seen in FIGS. 2, 5 and 7 there is a second concentric chamber 22 positioned radially outward from the pressure chamber 17. Referring back to FIGS. 1, 4 and 6 it can be seen that the chamber 22 is formed by a second sleeve 23 of distensible material which is sealed at its ends 24, 25 to the stem 14 and valve block 21 in a manner similar to sleeve 18.

Figure 8:
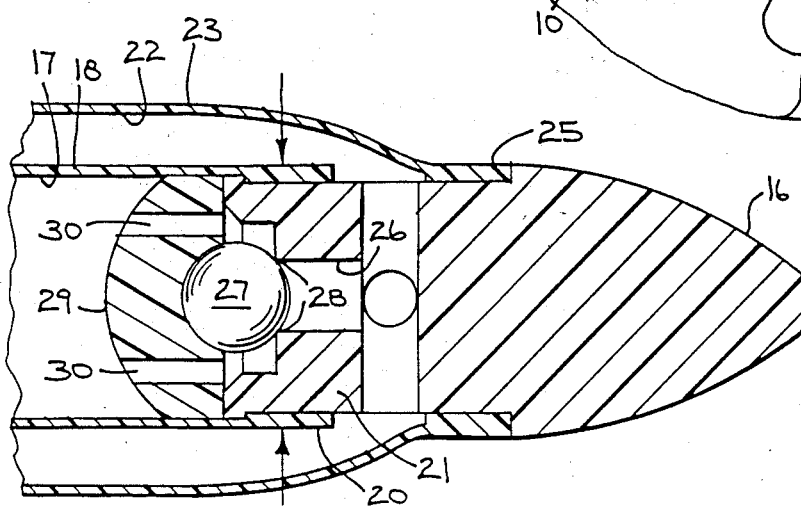
FIG. 8 is an enlarged sectional view of the top of the implant of FIG. 6.

As seen in FIG. 8, the chambers 17 and 22 are connected by a passage 26 which extends through the valve block 21. Liquid flow through the passage 26 is controlled by a first valve means which includes a ball 27, a ball seat 28 and a ball retaining member 29. The ball 27, which is normally kept seated on the seat 28 by the retainer 29, can be moved from its normal position closing the passage 26 to a position in which the passage is open to flow. When the ball 27 is off its seat 28 liquid can flow from the pressure chamber 17 through the passages 30 in the retainer 29 and the passage 26 into chamber 22. To facilitate the unseating of the ball 27 from the outside the valve block 21 is made of a relatively deformable plastic material.

Referring now to FIGS. 1, 4 and 6, it can be seen that communication between the pressure chamber 17 and the pressure bulb assembly 12 is provided by the length of tubing 13 and a passage 31 which passes throught the solid stem 14.

The pressure bulb assembly 12, which can be implanted in the scrotal sac of a patient, includes a pressure bulb 32 and a valve 33 for controlling the flow of pressurizing fluid between the pressure bulb 32 and the pressure chamber 17. The valve 33 preferably is normally closed but it can be opened manually be squeezing the pressure bulb 32 or the housing of the valve 33. The valve 33 is of the type which normally closes when the squeezing pressure on the bulb 32 stops or it can be of the type that does not completely close but delays the return of fluid to the bulb for a suitable period of time. Suitable valves are known and disclosed in U.S. Pat. Nos. 4,009,711 and 4,060,080.

Referring specifically now to FIG. 1, it can be seen that when the chamber 17 of the implant is depressurized the soft, relatively flexible distal portion 15 of the member 11 permits the penis to assume a substantially normal, flaccid position. In the preferred embodiment, as seen in FIG. 2 even in the flaccid position both chambers 17 and 22 are partially filled with pressurizing fluid 34.

Referring now to FIGS. 4 and 5, it can be seen that when the chamber 17 is pressurized the soft, flexible distal portion 15 of the member 11 is supported by the pressurized chamber 17 and the penis assumes a substantially normal erectile form. In the erectile form the pressure chamber 17 is completely filled and the distensible outer chamber 22 contains some pressurizing fluid 34. The non-distensible pressure chamber 17 is made rigid by simply squeezing the pressure bulb 32 which opens valve 33 and permits pressurizing fluid 34 to fill the chamber 17.

Referring now to FIGS. 6 and 7 the use of the implant 10 to increase penile girth will be described. As seen in FIG. 6 if the first valve is opened by deforming the block 21 and the pressure bulb 32 is simultaneously squeezed to open the second valve 33 pressurizing liquid will flow via passage 31 into the inner cylinder 17 and via passage 26 into the outer chamber 22 causing it to expand outwardly and increase penile girth. When the deformation of the valve block 21 is discontinued the passage 26 is closed and the liquid 34 which has been added is retained in the chamber 22. The girth increasing additional liquid in chamber 22 can be transferred back to chamber 17 by opening valve by deforming the valve block 21 and squeezing the distal portion 17 of the implant while opening the valve 33.

Figure 3:
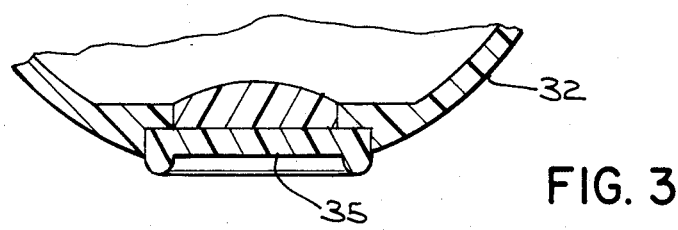
FIG. 3 is an enlarged sectional view of the bottom of the pressure blub of FIG. 1.

The pressure bulb 32 which is of flexible resilient material is provided with a one-way valve 35, seen best in FIG. 3, so that additional fluid can be added to the pressure bulb 32 with a hypodermic needle even after the implant 10 has been implanted. This may be necessary where the transfer of liquid to increase the girth to the desired level is too great to permit the desired erection. The valve 35 as shown in a resealable wall but, it can take other forms.

When it is desired to return the implant 10 to the non-pressurized form seen in FIG. 1 the valve 33 is opened to permit the pressurizing fluid 34 to be drained from the chamber 17 back via the passage 31 and tubing 13 through the valve 33 into the pressure bulb 32. Once an adequate amount of fluid has been returned to storage in the pressure bulb 32 the penis will be flaccid. If desired, the valve 33 may be one which will automatically open when the pressure in the tubing 13 exceeds a predetermined level and close when the pressure drops below that level; if such a valve is used it is not necessary to manipulate the valve 33 open as previously described.

As seen in the drawings the proximal stem 14 of the penile implant 10 at all times is anchored in the root end of the corpus cavernosum, and the paraboloidal tip 16 is positioned in the glans end of the corpus cavernosum. As a result, the implant 10 is positioned correctly in the corpus cavernosum of the penis and the likelihood of displacement is minimized.

Although in the drawings a single penile implant 10 is shown, the complete penile prosthesis will normally include two separate penile implants each sharing a common pressurizing bulb which is surgically implanted in the scrotal sac.

In the preferred embodiment of the invention, the proximal portion 14 of the member 11 has a Shore hardness of about 70, and the material has sufficient tensile strength for its intended use. Although a material of the described characteristics is preferred, any material which performs satisfactory under conditions of use can be employed.

The sleeve 18 is preferably made of a silicone elastomer coated woven or knit fabric which provides to a limited pre-determined expansion to allow the penis to become longer and to contain the pressure so that the tunica albuginea will not distend. Alternatively, the sleeve 18 also can be made of a material which does not distend either axially or longitudinally.

The diameter of the sleeve 18 is sufficient to form a functional pressure chamber 17. The use of a sleeve material which does not distend or distends only to a limited extent makes it possible to raise the fluid pressure in the chamber 17 to the desired high level with only a minimum of pressurizing fluid. The sleeve 23 may be made of unreinforced silicone rubber or any functionally equivalent or superior material.

The preferred method of implantation of implant 10 is through the perineum. After appropriate incision, the corpus cavernosum is dilated distally and proximally to accept the implant. The approximate anatomical measurements are made to insure that the proximal portion 14 of implant 10 will be positioned at the base of the penis below the pelvic bone. An implant having an appropriately sized distal portion 15 is obtained and the distal portion inserted into the corpus cavernosum of the penis. The proximal stem 14 of implant 10 is cut to the appropriate length. During the manufacture of implant 10 the length of proximal stem 14 may be deliberately made longer than necessary thereby permitting it to be trimmed to the correct length at the time of surgery. Only one implant of each distal portion length need, therefor, be available since other anatomical size variations may be accommodated by trimming proximal stem 14. This greatly reduces the number of implant sized which must be produced over that which would be required if no such size alteration were possible.

Proximal stem 14 is inserted in the dilated crus after trimming. The incision is then closed. The identical procedure is performed on the other side of the penis to complete the surgical procedure. The stems 14 of the two implants may diverge laterally to accommodate the anatomy and provide lateral stability to the penis.

In the preferred embodiment, all the parts and components of the prosthesis are made of medical application silicone rubber which is non-reactive, non-toxic and well tolerated by the adjacent organic tissues. Silicon rubber is preferred because it is quite resistant to wear and tear and remains functional for long periods of time. However, other suitable materials may be employed, if desired.

It will be readily apparent to those skilled in the art to which this invention relates that a variety of changes and modifications might be made without departing from the spirit and scope of the invention.

For example, although in the drawing the stem 14 is provided with a passage 31 that communicates with the pressure chamber 17 so that fluid can flow from the bulb 32 through the bore and indirectly into the pressure chamber other constructions could be used; the tubing 13 could communicate with the chamber 17 through a port extending through the walls of the chambers 17 and 22.

Furthermore, if desired, the sleeves 18 and 23 may take the initial shape of curved tubular members as opposed to the straight cylinders described and shown in the drawings. The forming of curved tubular sleeves in approximatedly the shape that the sleeves assume when the implant is in the depressurized state minimizes the likelihood of folds forming which can be encapsulated by scar tissue. However, in order to permit the curved tubular sleeve to assume the shape of a cylinder upon pressurization, it may be necessary to have selected longitudinal threads of the woven or knit fabric of the sleeve crimped to permit a limited longitudinal extension.

From the foregoing, it will be apparent that the description has been for purposes of illustration and is not intended to be limiting. For example, although an implant with an anchoring stem has been described it will be appreciated that other anchoring means can be used, if desired. Furthermore, although the preferred embodiment uses a common pressure bulb for two separate cylinders, other embodiments could employ one pressure bulb for each cylinder. Therefore, it is intended that the invention not be limited except by the claims which follow:

We claim:

1. In a penile prosthesis having a non-distensible pressure chamber for implantation in the pendulous penis, a pressure bulb for implantation in the scrotum, a length of tubing connecting the pressure bulb to the pressure chamber and a valve for controlling the flow of pressurizing fluid from the bulb to the chamber, the improvement which comprises a distensible chamber concentric with and outside of the pressure chamber, a passageway connecting the pressure chamber to the distensible chamber and manually operable valve means for controlling fluid flow between the pressure chamber and the distensible chamber so that when the valve means is opened and the pressure bulb is squeezed fluid can flow into and expand the distensible chamber thereby increasing the girth of the pendulous penis.

2. A penile prosthesis of claim 1 in which there are two separate implants each with a pressure chamber for implanting into the corpora cavernosa of a pendulous penis, a single pressure bulb and tubing connecting the single pressure bulb to the pressure chambers.

* * * * *